(12) United States Patent
Kobayashi et al.

(10) Patent No.: US 9,693,741 B2
(45) Date of Patent: Jul. 4, 2017

(54) MAMMOGRAPHIC APPARATUS

(71) Applicant: Toshiba Medical Systems Corporation, Otawara (JP)

(72) Inventors: Yoshimasa Kobayashi, Nasushiobara (JP); Haruki Iwai, Otawara (JP); Rie Ochiai, Nasushiobara (JP); Koichiro Watanabe, Nasushiobara (JP); Kazunari Shima, Nasushiobara (JP)

(73) Assignee: Toshiba Medical Systems Corporation, Otawara (JP)

( * ) Notice: Subject to any disclaimer, the term of this patent is extended or adjusted under 35 U.S.C. 154(b) by 251 days.

(21) Appl. No.: 14/567,686

(22) Filed: Dec. 11, 2014

(65) Prior Publication Data

US 2015/0157282 A1 Jun. 11, 2015

(30) Foreign Application Priority Data

Dec. 11, 2013 (JP) .................................. 2013-256500

(51) Int. Cl.
*A61B 6/00* (2006.01)
*A61B 6/04* (2006.01)

(52) U.S. Cl.
CPC ............ *A61B 6/0414* (2013.01); *A61B 6/502* (2013.01); *A61B 6/4035* (2013.01); *A61B 6/4233* (2013.01)

(58) Field of Classification Search
CPC .......... A61B 6/502; A61B 6/0414; A61B 6/04; A61B 6/4233
See application file for complete search history.

(56) References Cited

U.S. PATENT DOCUMENTS

2008/0101537 A1* 5/2008 Sendai .................. A61B 6/025
378/23

FOREIGN PATENT DOCUMENTS

JP 2010-142328 7/2010

* cited by examiner

*Primary Examiner* — Hoon Song
(74) *Attorney, Agent, or Firm* — Oblon, McClelland, Maier & Neustadt, L.L.P.

(57) ABSTRACT

A mammographic apparatus that includes X-ray detectors configured to detect X-rays entering the X-ray detectors, and attached to a holding-arm placed on a floor. The mammographic apparatus further includes circuitry configured to move the X-ray detectors between a scanning position and a waiting position. The X-ray detectors in the scanning position face an X-ray tube that generates X-rays across a breast-table, and the X-ray detectors in the waiting position are closer to the holding-arm than are the X-ray detectors in the scanning position.

12 Claims, 11 Drawing Sheets

MAMMOGRAPHIC APPARATUS

CROSS-REFERENCE TO RELATED APPLICATIONS

This application is based upon and claims the benefit of priority from prior Japanese Patent Application No. 2013-256500, filed Dec. 11, 2013, the entire contents of which are incorporated herein by reference.

FIELD

Embodiments herein relate to a mammographic apparatus for taking an image of a breast by detecting the X-ray radiated from an X-ray tube and transmitted through a breast of a subject by an X-ray detector.

DESCRIPTION OF THE RELATED ART

Nowadays, a test for breast cancer is broadly used for finding a breast tumor. An X-ray technician scans a test-subject's breast using a mammographic apparatus, as the test for breast cancer. A radiologist checks X-ray images scanned by the mammographic apparatus, and gives a diagnosis of breast cancer.

In order to find a lesion such as a calcification or a tumor from the breast, and to give a diagnosis of breast cancer, a mammographic apparatus should scan an entire area of the breast. To ensure the scanning of the entire area of the breast, the mammographic apparatus can scan the breast from two-directions. By scanning from two-directions and getting two X-ray images, the radiologist can find the lesion from one of the X-ray images, even if the other X-ray image does not visualize the lesion, which may be under a milk line of the breast. Generally, one of the two-directions is called an MLO (Medio-lateral Oblique), and another direction is called a CC (Cranio-Caudal).

In order to scan the breast using the mammography apparatus, the X-ray technician first places the breast of the test-subject on a breast-table. Then the X-ray technician presses the breast using a pressure-pad to fix the breast in place. When the X-ray technician scans the breast from the CC direction, as the first step, the X-ray technician rotates a holding arm. The holding arm has an X-ray tube at the top position, the breast-table and X-ray detectors at the bottom position, and the pressure-pad at the middle position. As the next step, the X-ray technician pulls the breast towards the breast-table, and pushes up fat tissues of the breast. When the X-ray technician scans the breast from the MLO direction instead of the CC direction, the X-ray technician rotates the holding arm and makes it being slanted. Then the X-ray technician places the breast on the breast-table that is slanted by the rotated holding arm. Next, the X-ray technician spreads out the breast in order to maintain the breast at a uniform height. As a next step, the X-ray technician presses the flattened breast by moving the pressure-pad. As the final step, the X-ray technician fixes the position of the pressure-pad and releases his/her hands from the breast, and then the X-ray technician finishes fixing the position of the breast.

FIG. 11 shows the X-ray tube and the X-ray detectors. The X-ray tube is located at the upper side of the holding arm, and the X-ray detectors are located at the bottom side of the holding arm. As FIG. 11 shows, a box accommodates the X-ray tube (this box accommodating the X-ray tube is called a "head-portion" in the present disclosure) located in front of the pressure-table and the pressure-pad. Thus, when the X-ray technician scans the breast from the MLO direction, the X-ray technician has to crawl under the head-portion and to fix the position of the breast. In this case, the X-ray technician has to keep a low posture in order to avoid colliding his/her head with the head-portion.

Further, when the X-ray technician scans the breast from the CC direction, the head-portion is located in front of the head of the test-subject. Then, the head of the test-subject may have a feeling of pressure by the head-portion.

SUMMARY

The present embodiments have been made in consideration of the above situation, and provide a mammographic apparatus that can effectively test for breast cancer.

In one embodiment, a mammographic apparatus includes a breast-table configured to support a breast of a test-subject, a pressure-pad that is translucent, and is configured to press the breast on the breast-table, and an X-ray tube configured to generate X-rays towards the breast-table, the X-ray tube facing the pressure-pad across the breast-table. The mammographic apparatus also includes X-ray detectors configured to detect the X-rays going through the breast-table and the pressure-pad, a holding-arm configured to support the breast-table, the pressure-pad, and the X-ray tube, and a detector moving circuit attached to the holding-arm, and configured to move the X-ray detectors between a scanning position and a waiting position. Further, in the mammographic apparatus, the X-ray detectors in the scanning position face the X-ray tube across the breast-table and the pressure-pad, and the X-ray detectors in the waiting position are closer to the holding-arm than are the X-ray detectors in the scanning position.

DETAILED DESCRIPTION

Figure 1:
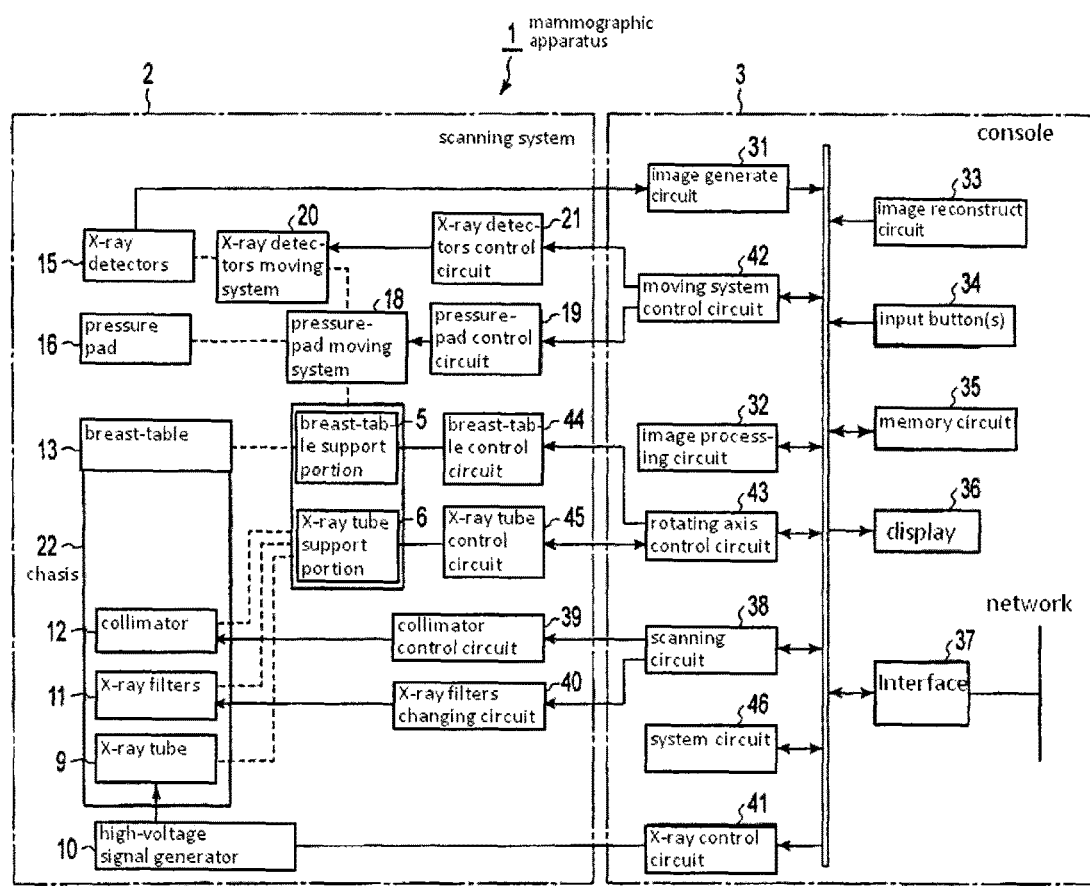
FIG. 1 is a block diagram of a mammographic apparatus according to an embodiment.

Embodiments of the present disclosure will be described below with reference to the views of the accompanying drawings. Note that the same reference numerals denote constituent elements having substantially the same functions and arrangements, and a repetitive description will be made only when required.

FIG. 1 is a block diagram of a mammographic apparatus 1. As shown in FIG. 1, the mammographic apparatus 1 has a scanning system 2 and a console 3.

Figure 2:
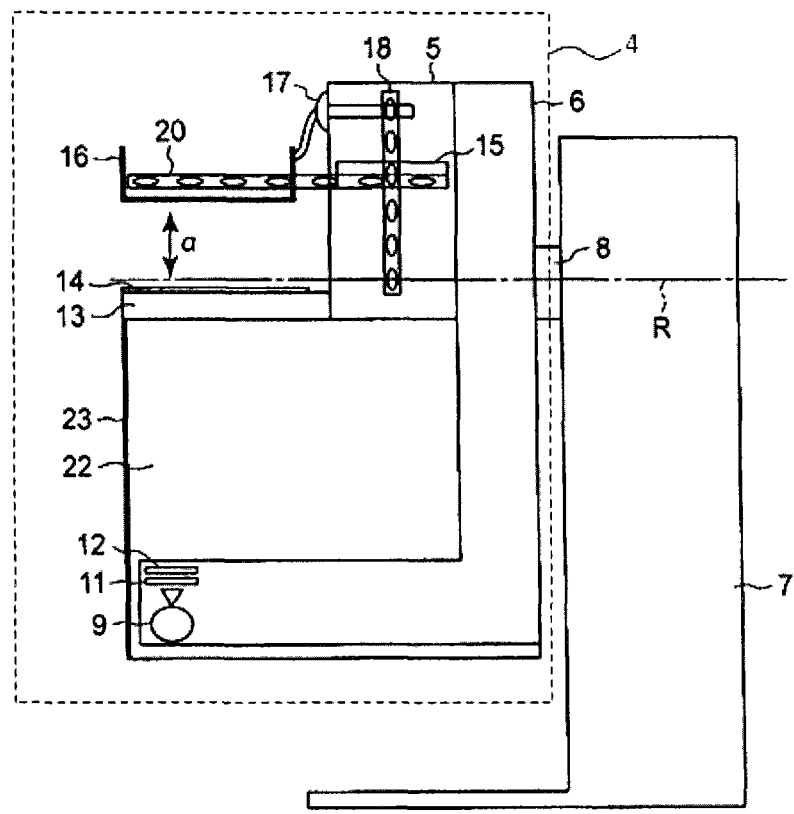
FIG. 2 is a cross-section diagram of the mammographic apparatus according to an embodiment.

FIG. 2 is a cross-sectional diagram of the mammographic apparatus 1. The scanning system 2 has a holding arm 4. The holding arm 4 has a breast-table support portion 5 and an X-ray tube support portion 6. The breast-table support portion 5 and the X-ray tube support portion 6 are fixed to a rotating axis 8. The rotating axis 8 is connected to a base-post 7 in an orthogonal manner. The rotating axis 8 is shown in FIG. 2. The breast-table support portion 5 and the X-ray tube support portion 6 can separately rotate with respect to the base-post 7, the rotation center being the rotating axis 8. By rotating the breast-table support portion 5 and the X-ray tube support portion 6, the mammographic apparatus can change a scan-direction between the MLO direction and the CC direction.

An X-ray tube 9 is fixed at an end of the X-ray tube support portion 6. The X-ray tube 9 is connected to a high-voltage signal generator 10, and the X-ray tube 9 radiates X-rays when the X-ray tube 9 receives electric signal with high voltage and current from a high-voltage signal generator 10. Plural X-ray filters 11 are attached to the X-ray tube 9, and an energy spectrum of the X-ray from the X-ray tube 9 is changed by swapping the X-ray filters 11 attached to the X-ray tube 9. Further, a collimator 12 is attached to the X-ray tube 9, the collimator 12 limiting an area of radiating X-ray.

A breast-table 13 is fixed at an end of the breast-table support portion 5. The breast of the test subject is placed on a top plane 14 of the breast-table 13.

When the X-ray tube 9 is located at the lowest part of the holding arm 4, a rotation-degree of the X-ray tube support portion 6 is defined as 0 degrees. When the rotation-degree of the breast-table support portion 5 is 0, the top plane 14 is parallel to a floor that the mammographic apparatus 1 is placed on. A rotation-degree of the breast-table support portion 5 can be changed. The test subject can place the breast on the breast-table 13 in a stable manner. For ease of explanation, the rotation-degree of the breast-table support portion 5 is fixed to 0, when the mammographic apparatus 1 scans the breast towards the CC direction.

Note that FIG. 2 is a diagram of the mammographic apparatus 1, when the rotation-degree of the X-ray tube support portion 6 is 0 degrees. When the rotation-degree of the X-ray tube support portion 6 is 0 degrees, the mammographic apparatus 1 can scan the breast through the CC direction. In this situation, the X-ray tube 9 and the breast-table 13 face each other across a pressure-pad 16, and the X-ray tube 9 and X-ray detectors 15 face each other across the breast-table 13 and the pressure-pad 16.

Figure 3:
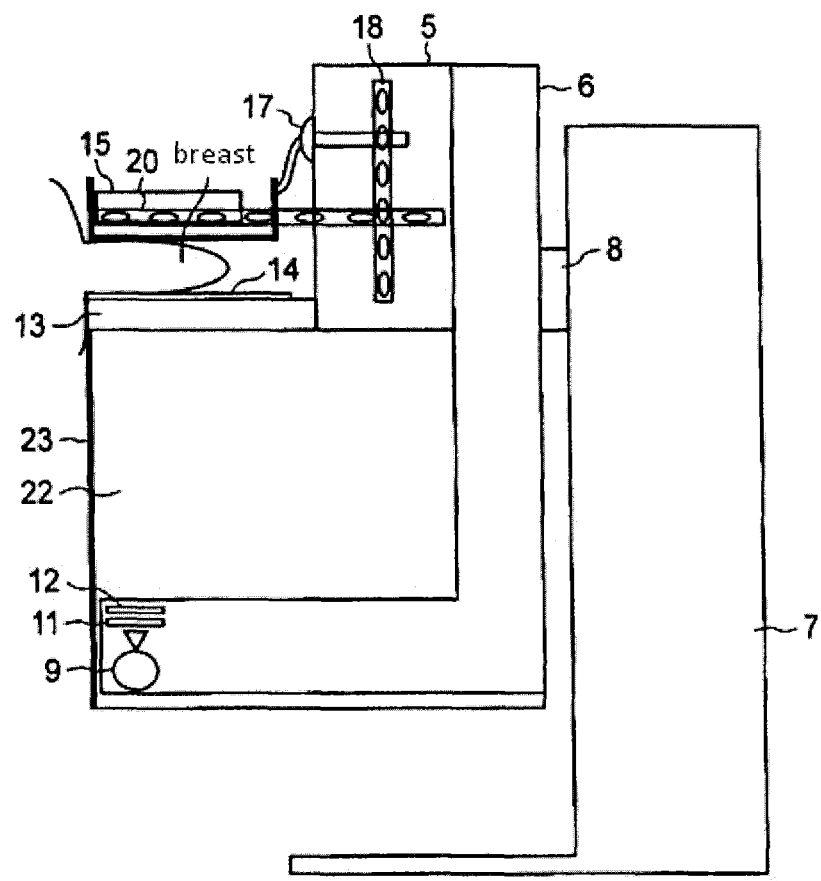
FIG. 3 is a diagram showing a positional relationship of the X-ray tube and the X-ray detectors according to an embodiment.
Figure 11:
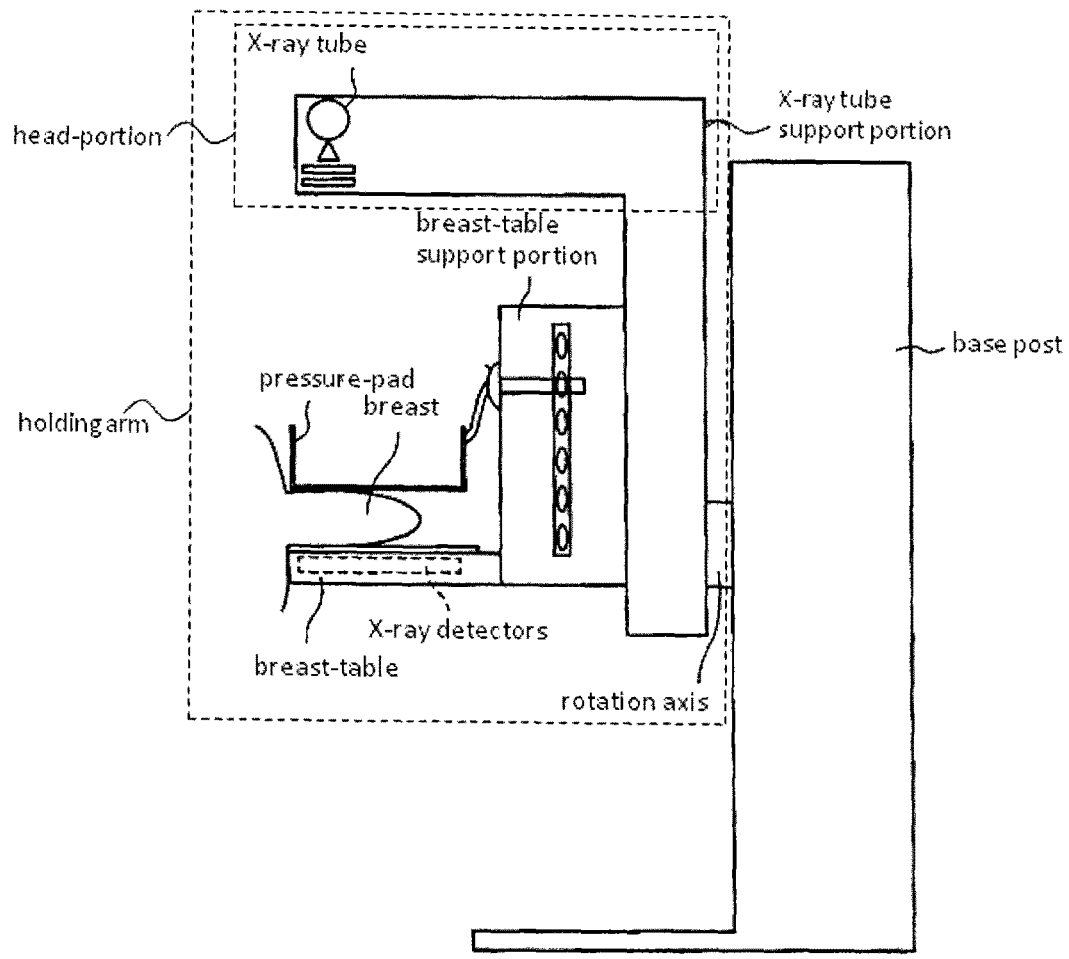
FIG. 11 is a diagram showing a positional relationship of the X-ray tube and the X-ray detectors according to the related art.

FIG. 3 is a diagram showing a positional-relationship of the X-ray tube 9 and the X-ray detectors 15. From bottom to top, the X-ray tube 9, the breast-table 13, the top-plane 14, the breast of the test subject, the pressure-pad 16, and the X-ray detectors 15 are located in line. That is, in the mammographic apparatus 1 according to this embodiment, the X-ray tube 9 and the X-ray detectors 15 are located in a reverse manner from the mammographic apparatus of the related art shown in FIG. 11. In the mammographic apparatus 1 of the present embodiment, the X-ray tube 9 is located under the breast-table 13, and then the head-portion accommodating the X-ray tube 9 can avoid being in front of a face of the test subject and the X-ray technician.

When the mammographic apparatus 1 scans the breast through the MLO direction, the rotation-degree of the breast-table support portion 5 is set to −1 to −60 degrees, and the rotation-degree of the X-ray tube support portion 6 is set to 1 to 60 degrees. When the breast scanned by the mammographic apparatus 1 is switched to another breast, the rotation-degree of the breast-table support portion 5 is set to 1 to 60 degrees, and the rotation-degree of the X-ray tube support portion 6 is set to −1 to −60 degrees. In a same manner to the CC direction, in the mammographic apparatus 1, since the X-ray tube 9 is located under the breast-table 13, the head-portion can avoid being in front of the face of the test subject and the X-ray technician.

The X-ray detectors 15 comprise one or more FPDs (Flat Panel Detectors). The FPD has detection-elements aligned on a grid. Each of the detection-elements detects the X-ray radiated from the X-ray tube 9, and converts it into electronic signals. Each of the detection-elements outputs the electronic signals into an ADC (Analog to Digital Converter). The ADC converts the electronic signals from the detection-elements into digital signals. The ADC outputs the digital signals into an image generation circuit 31.

The pressure-pad 16 is fixed to a pressure-pad moving system 18. The pressure-pad moving system 18 moves the pressure-pad 16, and brings the pressure-pad 16 close to the breast-table 13, or separates the pressure-pad 16 from the breast-table 13. In details, a pressure-meter 17 is connected to the pressure-pad 16, and the pressure-meter 17 detects an amount of pressure between the pressure-pad 16 and the breast of the test subject. The pressure-meter 17 generates pressure-signals representing an amount of the pressure, and the pressure-meter 17 outputs the pressure-signals into the system circuit 46.

The pressure-pad moving system 18 is located inside of the breast-table support portion 5, and supports the pressure-pad 16 and the pressure-meter 17. The pressure-pad moving system 18 moves the pressure-pad 16 towards the breast-table 13. As shown in FIG. 2, the pressure-pad moving system 18 moves the pressure-pad 16 along direction alpha (α). When the pressure-pad moving system 18 brings the pressure-pad 16 close to the breast-table 13, the breast of the test subject is compressed like a slab.

The pressure-pad moving system 18 comprises a ball screw attached to the pressure-pad 16, a guide rail, a first slider which extends along with the direction alpha, and a motor which screws the ball screw. One end of the ball screw is connected to the breast-table supporting portion 5. A ball of the ball screw is moved along an axis of the ball screw, when the axis is rotated. The guide rail and the axis of the ball screw are placed in parallel and are fixed at the breast-table support portion 5. The first slider is connected to the ball of the ball screw. When the axis of the ball screw is rotated, the ball of the ball screw pushes the first slider connected to the ball screw along the axis of the ball screw. In a same manner as the pressure-pad moving system 18, an X-ray detectors moving system 20 comprises a ball screw, a guide rail, and a second slider. When the axis of the ball screw is rotated, the ball of the ball screw pushes the second slider connected to the ball screw along the axis of the ball screw.

When the axis of the ball screw of the pressure-pad moving system 18 is rotated, the first slider moves along the guide rail. The X-ray detectors moving system 20 and the pressure-pad 16 are fixed to the pressure-pad moving system 18. So when the first slider moves along the guide rail, the X-ray detectors moving system 20 and the pressure-pad 16 move towards the breast-table 13, or away from the breast-table 13. The X-ray detectors 15 are fixed to the second slider of the X-ray detectors moving system 20. Thus, when the second slider moves along the guide rail, the X-ray detectors 15 are pulled out from the breast-table support portion 5.

The pressure-meter 17 is connected to the pressure-pad 16. The pressure-meter 17 can be located outside of the breast-table support portion 5. The pressure-meter 17 detects the amount of pressure between the pressure-meter 17 and the breast of the test subject. The X-ray detector moving system 20 moves the X-ray detectors 15 in a direction perpendicular to the direction alpha (the axis of the first slider).

The X-ray detectors moving system 20 moves the X-ray detectors 15 between two positions, a scanning position and a waiting position. When the X-ray detectors 15 are in the scanning position, the X-ray detectors 15 are located above the pressure-pad 16, and the X-ray detectors 15 are in the radiation-range of the X-ray tube 9. That is, the X-ray detectors 15 in the scanning position face the X-ray tube 9 across the breast-table 13 and the pressure-pad 16. The X-ray detectors 15 can also be inside of the pressure-pad 16 in the scanning position.

When the X-ray detectors 15 are in the waiting position, the X-ray detectors 15 are located inside of the breast-table support portion 5, and the X-ray detectors 15 are out from the radiation-range of the X-ray tube 9. That is, the X-ray detectors 15 in the waiting position are closer to the holding-arm 4 than are the X-ray detectors 15 in the scanning position. The X-ray detectors 15 can also be above the breast-table support portion 5 in the scanning position.

As described above, the X-ray detectors moving system 20 comprises the ball screw attached to the X-ray detectors 15, the guide rail, the second slider, and a motor which screws the ball screw. The ball screw and the guide rail are connected to the breast-table support portion 5, and the guide rail is placed perpendicular to the direction alpha. When the axis of the ball screw is rotated by the motor, the second slider connected to the ball of the ball screw moves along the axis of the ball screw.

An X-ray detectors control circuit 21 is connected to the motor of the X-ray detectors moving system 20. When the X-ray detectors control circuit 21 drives the motor, for rotating the axis of the ball screw, the second slider and the X-ray detectors 15 connected to the second slider move along the axis of the ball screw. By moving the second slider, the X-ray detectors 15 change positions between the scanning position and the waiting position.

Figure 4:
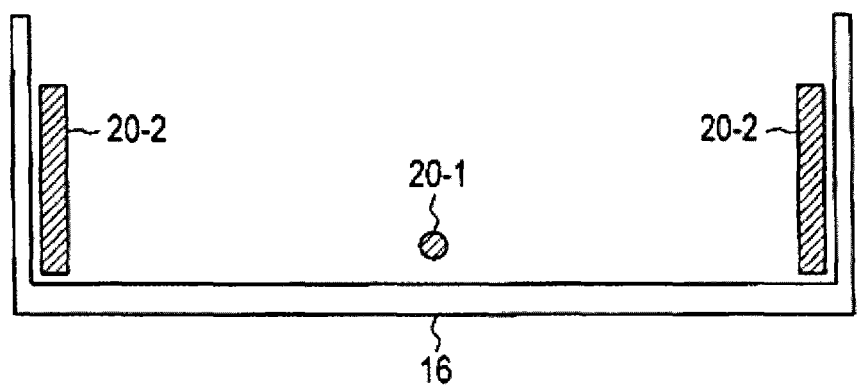
FIG. 4 is a diagram showing a positional relationship of the pressure-pad and a moving system according to an embodiment.

FIG. 4 is a cross-section diagram of the pressure-pad 16, showing a positional-relationship of the pressure-pad 16 and the X-ray detectors moving system 20. The cross-section is perpendicular to the rotation axis of the holding arm 4. As shown in the FIG. 4, the ball screw 20-1, the guide rail 20-2, and the guide rail 20-2 have a distance from inner walls of the pressure-pad 16.

In general, the pressure-pad 16 is made out of a soft and elastic material such as plastic, in order to avoid pressing the breast of the test subject too hard. On the other hand, the ball screw 20-1, and the guide rails 20-2 and 20-2 are made out of hard and rigid material such as aluminum. When the hard material of the X-ray detectors moving system 20 contacts the inner wall of the pressure-pad 16, the pressure-pad 16 loses its elasticity by the inner hard material of the X-ray detectors moving system 20. However, if there is a big distance between the pressure-pad 16 and the X-ray detectors moving system 20, the X-ray detectors 15 separate from the breast of the test subject. The distance between the X-ray detectors 15 and the breast causes blurs in the X-ray images. Thus, the X-ray detectors moving system 20 should maintain adequate distance from the pressure-pad 16 in order to keep quality of the X-ray images.

A chassis 22 accommodates the X-ray tube 9 and the breast-table 13 with the top plane 14 of the breast-table 13 exposed. The chassis 22 is coated with an X-ray shield 23, in order to prevent the X-ray from going outside of the scan area. The X-ray shield 23 is made out of a metal material such as lead, which has a high absorption-rate of the X-ray. The X-ray shield 23 can shield every surface of the chassis 22, or can shield several surfaces of the chassis 22.

As noted above, the mammographic apparatus 1 comprises the scanning system 2 and the console 3. The console 3 has an image generate circuit 31, an image processing circuit 32, an image reconstruct circuit 33, an input button(s) 34, a memory circuit 35, a display 36, an interface circuit 37, a scanning circuit 38, an X-ray control circuit 41, a moving system control circuit 42, a rotating axis control circuit 43, and the system circuit 46.

The image generate circuit 31 generates the X-ray images, by processing the digital signals from the X-ray detectors 15. The image generate circuit 31 collects signal-imbalance among detectors of the X-ray detectors 15, and collects absence of the digital signals from the X-ray detectors 15. After collecting the digital signals, the image generate circuit 31 generates the X-ray images from the collected digital signals, then outputs the X-ray images to the image processing circuit 32.

The image processing circuit 32 processes the X-ray images from the image generate circuit 31. The image processing circuit 32 removes effects of scattered X-rays from the X-ray images. The image reconstruct circuit 33 reconstructs volume data from the X-ray images that are obtained by scanning from different directions.

The input button 34 inputs parameters regarding X-rays, position of scanning, and start and end time of scanning by the X-ray technician's operation. The input button 34 outputs the parameters and input signals to the system circuit 46.

The memory circuit 35 stores the input signals and the parameters from the input button 34. In addition, the memory circuit 35 stores the X-ray images from the image generate circuit 31 and the image processing circuit 32, and stores the volume data from the image reconstruct circuit 33. The memory circuit 35 outputs the X-ray images and the volume data to the display 36 and the interface circuit 37.

The display 36 displays information that is the X-ray images from the image generate circuit 31 and the image processing circuit 32. Furthermore, the display 36 can display images and parameters stored by the memory circuit 35. The interface circuit 37 connects PACS (Picture Archiving and Communication Systems) and computers through a network, and exchanges the images.

The scanning circuit 38 controls a collimator control circuit 39 and an X-ray filters changing circuit 40, and controls the scanning system 2 to scan the breast of the test subject. The collimator control circuit 39 moves the collimator 12 based on the input signal from the scanning circuit 38, in order to change the radiation area. The X-ray filters changing circuit 40 changes the X-ray filters 11 based on the input signal from the scanning circuit 38. Further, the X-ray control circuit 41 controls the high-voltage signal generator 10, based on the system circuit 46.

The moving system control circuit 42 controls a pressure-pad control circuit 19 and the X-ray detectors control circuit 21. The pressure-pad control circuit 19 drives the pressure-pad moving system 18, based on signals from the moving system control circuit 42. The pressure-pad moving system 18 moves the pressure-pad 16 based on driving signals from the pressure-pad control circuit 19. The X-ray detectors control circuit 21 drives the X-ray detectors moving system 20, based on signals from the moving system control circuit 42. The X-ray detectors moving system 20 moves the X-ray detectors 15 based on driving signals from the X-ray detectors control circuit 21.

The rotating axis control circuit 43 controls a breast-table control circuit 44. The breast-table control circuit 44 drives the breast table 5 based on the signal from the rotating axis control circuit 43. The breast-table control circuit 44 rotates the breast-table support portion 5, and changes the rotation degree of the breast-table 13. The rotating axis control circuit 43 controls an X-ray tube control circuit 45. The X-ray tube control circuit 45 rotates the X-ray tube support portion 6, and changes the rotation degree of the X-ray tube 9.

Further, note that the system circuit 46 controls all circuits connected to the system circuit, in order to scan the breast of the test subject.

Figure 5:
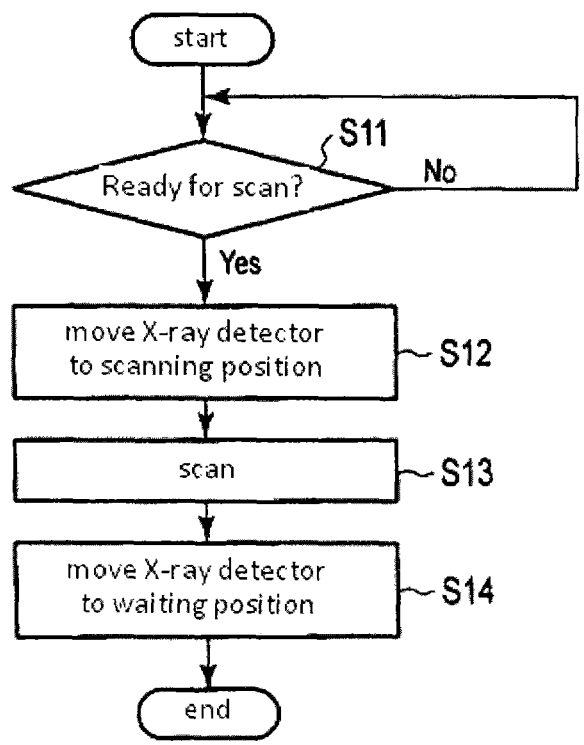
FIG. 5 is a flow-chart showing a flow of the test for breast cancer.

FIG. 5 is a flowchart showing a procedure of the test for breast cancer. The procedure of the test for breast cancer is described below with reference to FIG. 5.

In the first step, the system circuit 46 waits for an input signal to start a scan (step S11). When the X-ray technician finishes fixing the position of the breast, the X-ray technician operates the input button 34 and the input signal for starting the scan is sent to the system circuit 46. When system circuit 46 receives the input signal for starting the scan, the system circuit 46 proceeds to the next step, S12.

Figure 6:
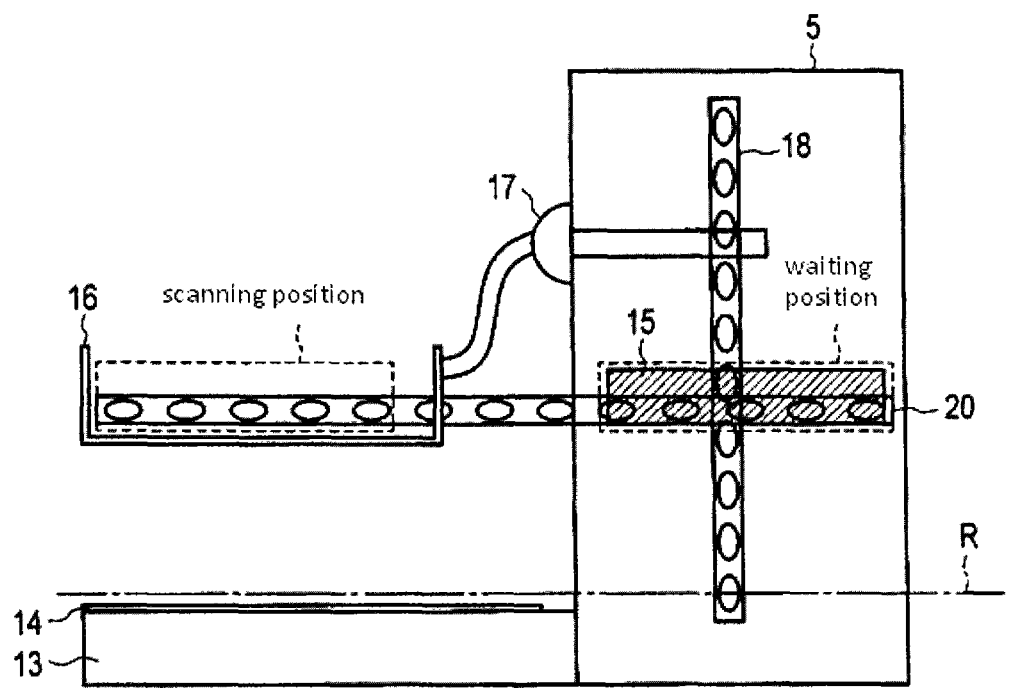
FIG. 6 is a diagram showing the location of the X-ray detectors in a waiting position.

When the X-ray technician scans the breast from the MLO direction, the X-ray technician has to place the breast on the top plane 14. In order to place the breast on the top plane 14, the X-ray technician rotates the breast-table support portion 5 to a predetermined rotation degree. Next, the X-ray technician pulls the breast towards the breast-table 13, and pushes up fat tissues of the breast. Then the X-ray technician places the breast on the breast-table 13 that is slanted by the rotated holding arm 4. Next, the X-ray technician spreads out the breast in order to keep the breast having a uniform height. Next, the X-ray technician presses the flattened breast by moving the pressure-pad 14. Finally, the X-ray technician fixes the position of the pressure-pad 14 and releases his/her hands from the breast, and then the X-ray technician finishes fixing the position of the breast. As shown in FIG. 6, the X-ray detectors 15 are in the waiting position when the X-ray technician places the breast on the top plane 14.

The pressure-pad 16 is made out of a translucent material such as plastic. In order to place the breast on the top plane 14, the X-ray technician checks the breast position by seeing the breast position through the pressure-pad 16. The X-ray detectors 15 are made out of the metal material, and are not translucent. Thus, if the X-ray detectors 15 are in the scanning position above the pressure-pad 16, the X-ray technician cannot check the breast position. Thus, in order to check the breast position, the X-ray detectors 15 have to be in the waiting position.

Figure 7:
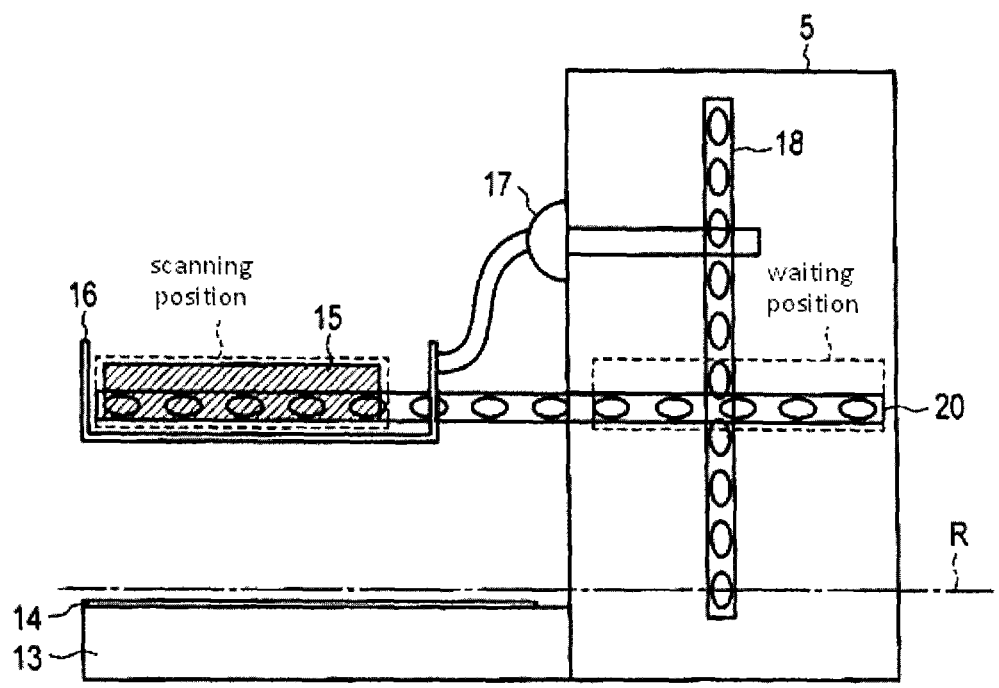
FIG. 7 is a diagram showing the location of X-ray detectors in a scanning position.

Next, the system circuit 46 controls the moving system control circuit 42. The moving system control circuit 42 drives the X-ray detectors moving system 20 to move the X-ray detectors 15 to the scanning position (S12). FIG. 7 is a diagram showing that the X-ray detectors 5 located at a scanning position. When the X-ray detectors 15 move to the scanning position as in S12, the X-ray technician operates the input button 34, and inputs the signal for scanning to the system circuit 46.

Next, the system circuit 46 controls the scanning system 2 to start the scan (S13). The scanning system 2 controls the high-voltage signal generator 10 to drive the X-ray tube 9. The X-ray tube 9 radiates the X-ray towards the breast and the X-ray detectors 15 at the scanning position. The system circuit 46 can scan the breast from plural directions, for executing a stereo scan or a tomosynthesis scan.

When the system circuit 46 executes the tomosynthesis scan, the system circuit 46 controls the scanning system 2, and scans the breast with the plural rotating degrees of the X-ray support portion 6. For example, the X-ray support portion 6 rotates from −15 degrees to +15 degrees, and the X-ray tube 9 radiates the X-ray towards the breast and the X-ray detectors 15 periodically when the X-ray support portion 6 is rotating. The image generate circuit 31 generates X-ray images corresponding to the plural scan directions.

Next, the system circuit 46 controls the moving system control circuit 42, and the moving system control circuit 42 drives the X-ray detectors moving system 20 to move the X-ray detectors 15 to the waiting position (S14). When the X-ray detectors 15 are moved to the waiting position, the X-ray technician operates the input button 34, and separates the pressure-pad 16 from the breast and the top plane 14.

As described above, the X-ray detectors 15 connected to the pressure-pad moving system 18 can move towards the breast-table 13 and away from the breast-table 13 when the X-ray detectors 15 move along the direction alpha. Thus, when the X-ray detectors 15 move along the direction alpha, SID (Source-Image Distance: SID is a parameter that represents an amount of distance between the X-ray tube 9 and the X-ray detectors 15) is changed. When the SID parameter is changed, the amount of the scattered X-ray entering the X-ray detector 15 is also changed.

For removing an effect of the scattered X-ray, the image processing circuit 32 collects the X-ray image generated by the image generate circuit 31. The image processing circuit 32 checks a signal value of the X-ray image for each pixel, and determines a standard value based on the signal value of the X-ray image. The image processing circuit 32 converts the X-ray image into a reduced image, by converting pixel values in excess of the standard value into a predetermined low value. The image processing unit 32 converts the reduced image into a scattered image, by applying a predetermined scatter-convert function to the X-ray image. The scatter-convert function is determined by parameters of the X-ray and the distance between the X-ray tube 9 and the X-ray detectors 15. Finally, the image processing circuit 32 subtracts the scattered image from the X-ray image, and stores the subtracted image as a finalized image.

As described above, the mammographic apparatus according to this embodiment places the X-ray tube 9 under the breast-table 13. Thus, when the X-ray technician places the breast on the top plane 14, the head-portion accommodating the X-ray tube 9 can avoid being in front of a face of the test subject and the X-ray technician. In this case, the X-ray technician does not need to crawl under the head-portion to fix the position of the breast. When the X-ray technician places the breast on the top plane 14, the X-ray detectors 15 are in the waiting position. Thus, the X-ray technician can check the breast position by seeing the breast through the translucent pressure-pad 16. Then the X-ray technician can execute the test scan of the breast effectively.

Modified embodiments of the present disclosure will be described below. Note that the same reference numerals denote constituent elements having substantially the same functions and arrangements, and a repetitive description will be made only when required.

Modified Embodiment 1

When the mammographic apparatus 1 scans the breast, the X-ray detectors moving system 20 brings the X-ray detectors 15 to the scanning position. As in the first embodiment, this movement starts when the X-ray technician operates the input button 34. However, the timing of moving the X-ray detectors 15 can be changed. In modified embodiment 1, the X-ray detectors moving system 20 moves the X-ray detectors 15 to the scanning position, if the pressure-meter 17 detects pressure in excess of a predetermined value for a predetermined time, and if the input button 34 receives no input for a predetermined time.

The mammographic apparatus 1 according to the modified embodiment 1 comprises a time-meter. The time-meter detects the time length that the input button 34 receives no input.

Figure 8:
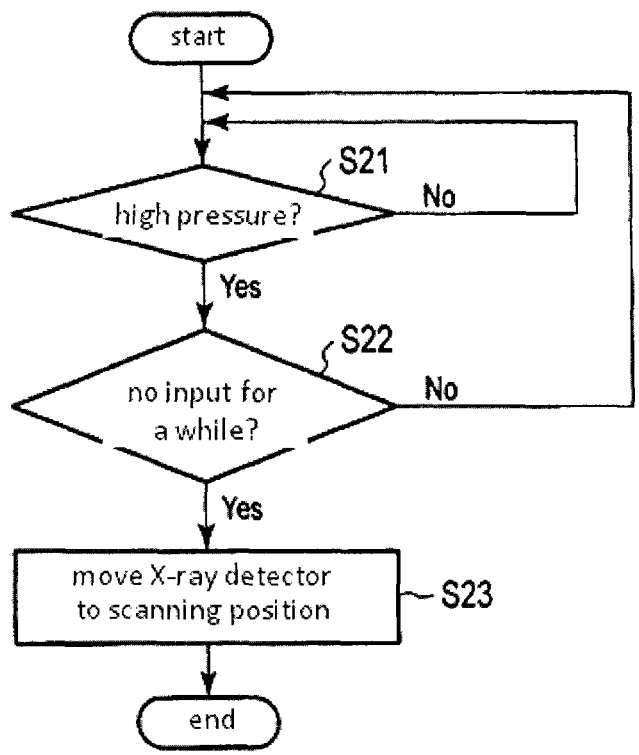
FIG. 8 is a flow-chart showing a process for moving the X-ray detectors according to a first modified embodiment.

FIG. 8 is a flow-chart showing a process for moving the X-ray detectors 15 according to the modified embodiment 1.

In a first step of the flow chart, the system circuit 46 checks an amount of the pressure-meter 17. The pressure-meter 17 periodically sends signals indicating the amount of the pressure between the pressure-pad 16 and the breast of the test subject to the moving system control circuit 42. The moving system control circuit 42 checks whether the amount of pressure is in excess of a predetermined threshold (S21). If the amount of pressure is in excess of the predetermined threshold, the system circuit 46 moves to S22.

Next, if the amount of pressure is in excess of the predetermined threshold, the system circuit 46 checks the time length that the input button 34 has received no input. The time-meter periodically sends signals indicating the time-length that the input button 34 receives no input to the system circuit 46. The system circuit 46 checks whether the time-length is in excess of a predetermined threshold (S22). If the time-length is in excess of the predetermined threshold, the system circuit 46 moves to S23.

Next, if the time-length is in excess of the predetermined threshold, the system circuit 46 controls the moving system control circuit 42. The moving system control circuit 42 moves the X-ray detectors 15 to the scanning position from the waiting position (S23).

As described above in the modified embodiment 1, the mammographic apparatus 1 moves the X-ray detectors 15 to the scanning position from the waiting position. This movement is executed automatically when the amount of pressure is in excess of the predetermined threshold, and when the time-length that the input button 42 has no input is in excess of the predetermined threshold. Such a situation means that the position of the breast on the top plane 14 is fixed. According to the modified embodiment 1, the X-ray technician does not need to operate the input button 42 for moving the X-ray detectors 15, and execute the scan effectively.

Modified Embodiment 2

As described in the modified embodiment 1, when the mammographic apparatus 1 scans the breast, the X-ray detectors moving system 20 brings the X-ray detectors 15 to the scanning position. As in the first embodiment, this movement starts when the X-ray technician operates the input button 34. However, the timing of moving the X-ray detectors 15 can be changed. In modified embodiment 2, the mammographic apparatus 1 comprises a human sensor. If the human sensor does not detect the X-ray technician, the X-ray detectors moving system 20 moves the X-ray detectors 15 to the scanning position.

The human sensor senses a position of the X-ray technician using infrared rays. The human sensor scans around the mammographic apparatus 1, except the area of the test subject. The area of the test subject is in front of the X-ray tube 9 and the X-ray detectors 15. The human sensor can be attached on a side of the holding arm 4, or the top of the holding arm 4. The human sensor senses a position of the X-ray technician by detecting an amount of pressure from the ground, instead of using the infrared rays. In this case, the human sensor is a pressure-sensor placed on the ground. Then, the pressure-sensor detects the number of pressure-point. If the pressure-sensor detects four (4) or more pressure-points, the human sensor assumes the test subject and the X-ray technician are on the pressure-sensor (that means 4 or more feet are on the pressure-sensor).

Figure 9:
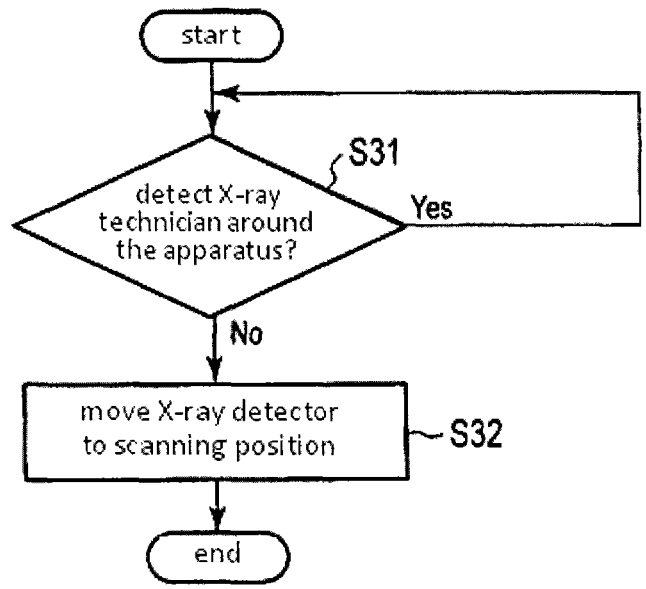
FIG. 9 is a flow-chart showing a process for moving the X-ray detectors according to a second modified embodiment.

FIG. 9 is a flow-chart showing a process for moving the X-ray detectors 15 according to the modified embodiment 2.

In the first step of the flow chart, the system circuit 46 checks whether the X-ray technician is around the mammographic apparatus 1 (S31). The human sensor periodically sends signals if the technician is around the mammographic apparatus 1 to the system circuit 46. If the system circuit 46 does not receive the signals from the human sensor for a while (a predetermined period of time), the system circuit 46 assumes that the X-ray technician has finished the breast position and has stepped away from the mammographic apparatus 1, and the system circuit 46 moves to S32.

Next, if the system circuit 46 assumes that the X-ray technician has left the area of the mammographic apparatus 1, the system circuit 46 controls the moving system control circuit 42, and the moving system control circuit 42 moves the X-ray detectors 15 to the scanning position from the waiting position (S32).

As described above in the modified embodiment 2, the mammographic apparatus 1 moves the X-ray detectors 15 to the scanning position from the waiting position. This movement is executed automatically when the system circuit 46 assumes that the X-ray technician finishes the breast position and leaves the area of the mammographic apparatus 1. According to the modified embodiment 2, the X-ray technician does not need to operate the input button 34 to move the X-ray detectors 15, and execute the scan effectively.

Modified Embodiment 3

As described in the modified embodiment 1, when the mammographic apparatus 1 scans the breast, the X-ray detectors moving system 20 brings the X-ray detectors 15 to the scanning position. As in the first embodiment, this movement starts when the X-ray technician operates the input button 34. However, the timing of moving the X-ray detectors 15 can be changed. In modified embodiment 3, the X-ray detectors moving system 20 brings the X-ray detectors 15 to the scanning position when the X-ray technician operates the console 3 and inputs the signal to start X-ray radiation to the system circuit 46.

Figure 10:
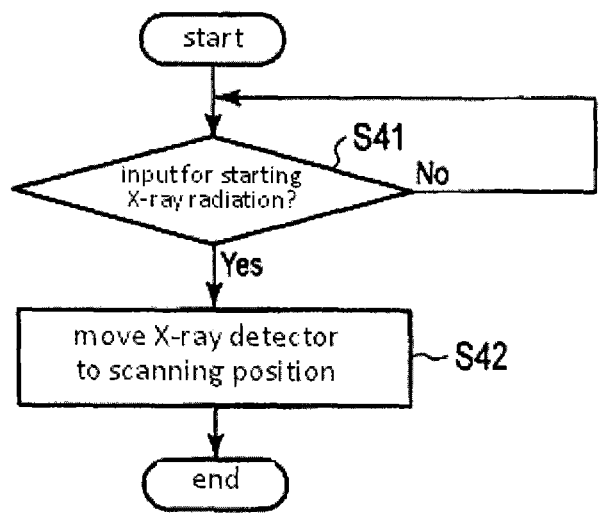
FIG. 10 is a flow-chart showing a process for moving the X-ray detectors according to a third modified embodiment.

FIG. 10 is a flow-chart showing a process for moving the X-ray detectors according to the modified embodiment 3.

In the first step, the system circuit 46 waits for a signal to start X-ray radiation from the console 3 (S41). Next, if the system circuit 46 receives the signal for starting X-ray radiation from the console 3, the system circuit 46 controls the moving system control circuit 42, and the moving system control circuit 42 moves the X-ray detectors 15 to the scanning position from the waiting position (S42). After moving the X-ray detectors 15, the X-ray tube 9 starts radiating the X-ray.

As described above in the modified embodiment 3, the mammographic apparatus 1 moves the X-ray detectors 15 to the scanning position from the waiting position. This movement is executed when the X-ray technician inputs the signal for starting X-ray radiation to the console 3. According to the modified embodiment 3, the X-ray technician does not need to operate the input button 34 for moving the X-ray detectors 15, and execute the scan effectively.

Modified Embodiment 4

As described above, the pressure-pad moving system 18 moves the pressure-pad 16 and the X-ray detectors 15 along the direction alpha. The X-ray detectors 15 can move towards and away from the breast-table 13. The suitable position of the X-ray detectors 15 will be varied by size and form of the breast of the test subject. For preventing variation of the SID parameter, an X-ray tube moving system can be attached to the X-ray tube 9. The X-ray tube moving system moves the X-ray tube 9 along the direction alpha by using sliders attached to the X-ray tube 9 and the holding-arm 4. Then, the X-ray tube 9 can move towards and away from the breast-table 13 in the same manner as the X-ray detectors 15. For example, if the X-ray detectors 15 move towards the breast-table 13 by a certain distance, the X-ray tube moving system moves the X-ray tube 9 away from the breast-table 13 by the same distance. On the other hand, if the X-ray detectors 15 move away from the breast-table 13 by a certain distance, the X-ray tube moving system moves the X-ray tube 9 towards the breast-table 13 by that same distance. By moving the X-ray tube 9 towards the direction alpha, the X-ray detector 15 can keep the same distance from the X-ray tube 9, and the scanning system 2 can scan the X-ray images with the same SID parameter.

Note that the X-ray tube 9 and the X-ray detectors 15 do not need to move simultaneously. In a first step, the pressure-pad moving system 18 moves the pressure-pad 16 and the X-ray detectors 15 based on the input signal from the input button 34. After the X-ray detectors 15 finish moving, the X-ray tube moving system moves the X-ray tube 9 in order to keep a predetermined distance from the X-ray detectors 15 when the X-ray technician inputs the signal for starting X-ray radiation.

Note that the present invention is not limited to the above embodiments, and constituent elements can be variously modified and embodied at the execution stage within the spirit and scope of the invention. In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

Further, the console 3, components of the console 3, the pressure-pad control circuit 19, the X-ray detectors control circuit 21, the breast-table moving circuit 44, and the X-ray tube control circuit 45 can be implemented by using a central processing unit (CPU), one or more microprocessors, an application-specific integrated circuit (ASIC), and/or a field programmable gate array (FPGA). These components described above can be implemented as several separated hardware circuits as shown in FIG. 1, and also can be integrated in a single hardware circuit.

The invention claimed is:

1. A mammographic apparatus comprising:
    a breast-table configured to support a breast of a test-subject;
    a pressure-pad that is translucent, and is configured to press the breast on the breast-table;
    an X-ray tube configured to generate X-rays towards the breast-table, the X-ray tube facing the pressure-pad across the breast-table;
    X-ray detectors configured to detect the X-rays going through the breast-table and the pressure-pad;
    a holding-arm configured to support the breast-table, the pressure-pad, and the X-ray tube; and
    a detector moving circuit attached to the holding-arm, and configured to move the X-ray detectors between a scanning position and a waiting position,
    wherein the X-ray detectors in the scanning position face the X-ray tube across the breast-table and the pressure-pad, and the X-ray detectors in the waiting position are closer to the holding-arm than are the X-ray detectors in the scanning position.

2. The mammographic apparatus according to claim 1, wherein
    the X-ray detectors in the scanning position are located inside the pressure-pad, and
    the X-ray detectors in the waiting position are located inside the holding-arm.

3. The mammographic apparatus according to claim 1, further comprising:
    an input button configured to generate an input signal when the input button receives an input operation,
    wherein the detector moving circuit moves the X-ray detectors from the waiting position to the scanning position when the input button generates the input signal.

4. The mammographic apparatus according to claim 1, further comprising:
    input buttons configured to generate an input signal when the input buttons receive an input operation;
    a time-meter configured to detect a time-length that the input buttons do not receive the input operation; and
    a pressure-meter attached to the pressure-pad, and configured to detect amount of pressure received by the pressure-pad,
    wherein the detector moving circuit moves the X-ray detectors from the waiting position to the scanning position when the amount of pressure exceeds a predetermined pressure-threshold, and the time-length exceeds a predetermined time-length-threshold.

5. The mammographic apparatus according to claim 1, further comprising:
    a human sensor configured to detect a person in a predetermined sensing area,
    wherein the detector moving circuit moves the X-ray detectors from the waiting position to the scanning position when the human sensor does not detect the person in the predetermined sensing area.

6. The mammographic apparatus according to claim 5, wherein
    the predetermined sensing area is around an area which the X-rays are radiated by the X-ray tube.

7. The mammographic apparatus according to claim 3, wherein
    the X-ray tube starts radiating the X-rays when the input button generates the input signal.

8. The mammographic apparatus according to claim 1, further comprising:
    an X-ray tube support portion configured to rotate the X-ray tube around the X-ray detectors, wherein
    the X-ray tube radiates the X-rays when the X-ray tube support portion rotates the X-ray tube.

9. The mammographic apparatus according to claim 1, further comprising:
    an X-ray tube moving control circuit configured to move the X-ray tube towards the breast-table and away from the breast-table; and
    a pressure-pad moving control circuit configured to move the pressure-pad and the X-ray detectors towards the breast-table and away from the breast-table,
    wherein the X-ray tube moving control circuit moves the X-ray tube in a direction opposite to a moving direction of the pressure-pad and the X-ray detectors.

10. The mammographic apparatus according to claim 9, wherein
    the X-ray tube moving control circuit moves the X-ray tube towards the breast-table, when the pressure-pad moving control circuit moves the pressure-pad and the X-ray detectors away from the breast-table, and
    the X-ray tube moving control circuit moves the X-ray tube away from the breast-table, when the pressure-pad moving control circuit moves the pressure-pad and the X-ray detectors towards the breast-table.

11. The mammographic apparatus according to claim 9, further comprising:
    input buttons configured to generate an input signal when the input buttons receive an input operation,
    wherein the X-ray tube moving control circuit moves the X-ray tube in order to keep a predetermined distance between the X-ray tube and the X-ray detectors in the scanning position when the input buttons generate the input signal.

12. A mammographic apparatus comprising:
    X-ray detectors configured to detect X-rays entering the X-ray detectors, and attached to a holding-arm placed on a floor; and
    circuitry configured to move the X-ray detectors between a scanning position and a waiting position, wherein
    the scanning position is in an X-rays irradiated area,
    the waiting position is out of the X-rays irradiated area and closer to the holding-arm than the scanning position,
    the X-ray detectors are in the scanning position under scanning, and
    the X-ray detectors in the scanning position face an X-ray tube that generates X-rays across a breast-table.

* * * * *